United States Patent [19]

Funk

[11] Patent Number: 4,727,330

[45] Date of Patent: Feb. 23, 1988

[54] METHOD AND APPARATUS FOR MEASURING THE ELECTRICAL CONDUCTIVITY OF A SUBJECT

[75] Inventor: Robert C. Funk, Auburn, Ill.

[73] Assignee: Conductivity Diagnostics Research, Auburn, Ill.

[21] Appl. No.: 689,597

[22] Filed: Jan. 7, 1985

[51] Int. Cl.⁴ .......................................... G01N 27/02
[52] U.S. Cl. .................... 324/445; 324/233; 128/734
[58] Field of Search ............... 324/233, 234, 236, 237, 324/445, 61 R, 65 P; 128/653, 734

[56] References Cited

U.S. PATENT DOCUMENTS

| | | | |
|---|---|---|---|
| 3,478,263 | 11/1969 | Hentschel | 324/233 |
| 3,676,772 | 7/1972 | Lee | 324/233 |
| 3,735,247 | 5/1973 | Harker | 324/34 R |
| 3,895,290 | 7/1975 | Audenard | 324/233 |
| 4,411,270 | 10/1983 | Damadian | 128/653 |
| 4,493,039 | 1/1985 | Gregory | 324/233 |

FOREIGN PATENT DOCUMENTS

| | | | |
|---|---|---|---|
| 637973 | 3/1962 | Canada | 324/233 |
| WO81/03226 | 11/1981 | PCT Int'l Appl. | |
| 2140564 | 11/1984 | United Kingdom | 324/233 |

OTHER PUBLICATIONS

Tarjan: "Electrodeless Measurements . . . ", IEEE Transactions on BioMedical Eng.—Oct. 1968—pp. 266–277.

Primary Examiner—Reinhard J. Eisenzopf
Assistant Examiner—Jose M. Solis
Attorney, Agent, or Firm—Trexler, Bushnell, Giangiorigi & Blackstone, Ltd.

[57] ABSTRACT

Apparatus for measuring the electrical conductivity of a subject comprises a coil for producing a substantially uniform magnetic field within a predetermined volume and a transport assembly for causing relative movement between the subject and the predetermined volume so as to move at least portions of the subject into and out of the volume. A measuring circuit is coupled with the coil for measuring the electrical conductivity thereacross and a control circuit causes the measuring circuit to measure the electrical conductivity across the coil a plurality of times during movement of the subject relative to the volume so as to obtain a plurality of measurements of the electrical conductivity across the coil with different portions of the subject within the volume. A method for measuring the electrical conductivity of a subject comprises producing a substantially uniform magnetic field within a predetermined volume; causing relative movement between said subject and said predetermined volume so as to move at least portions of said subject into and out of said volume; measuring the electrical conductivity across said magnetic field a plurality of times during movement of said subject relative to said volume so as to obtain a plurality of measurements of the electrical conductivity across said magnetic field with different portions of said subject within said volume.

34 Claims, 14 Drawing Figures

Microfiche Appendix Included
(2 Microfiche, 94 Pages)

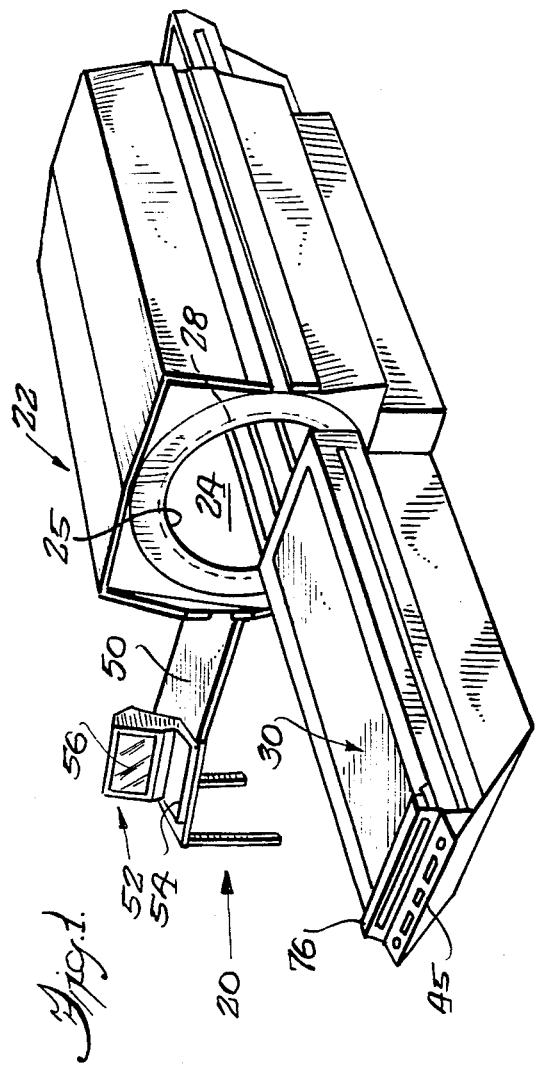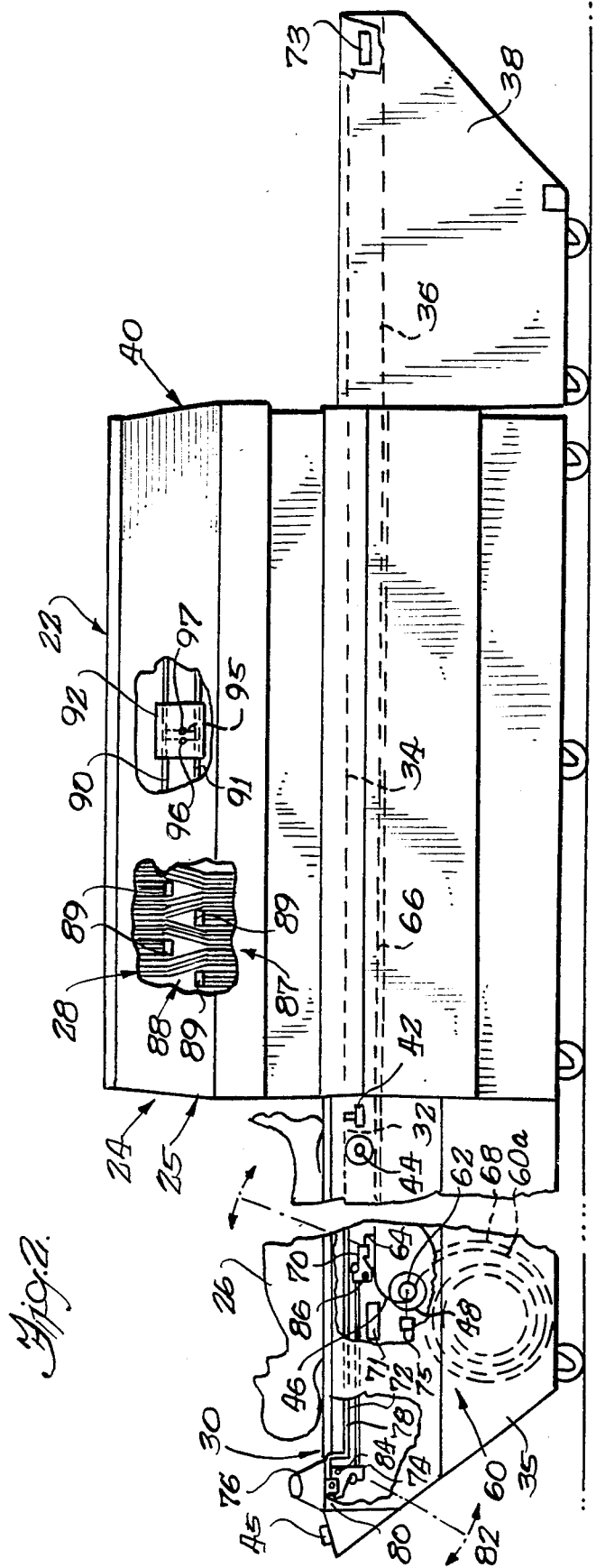

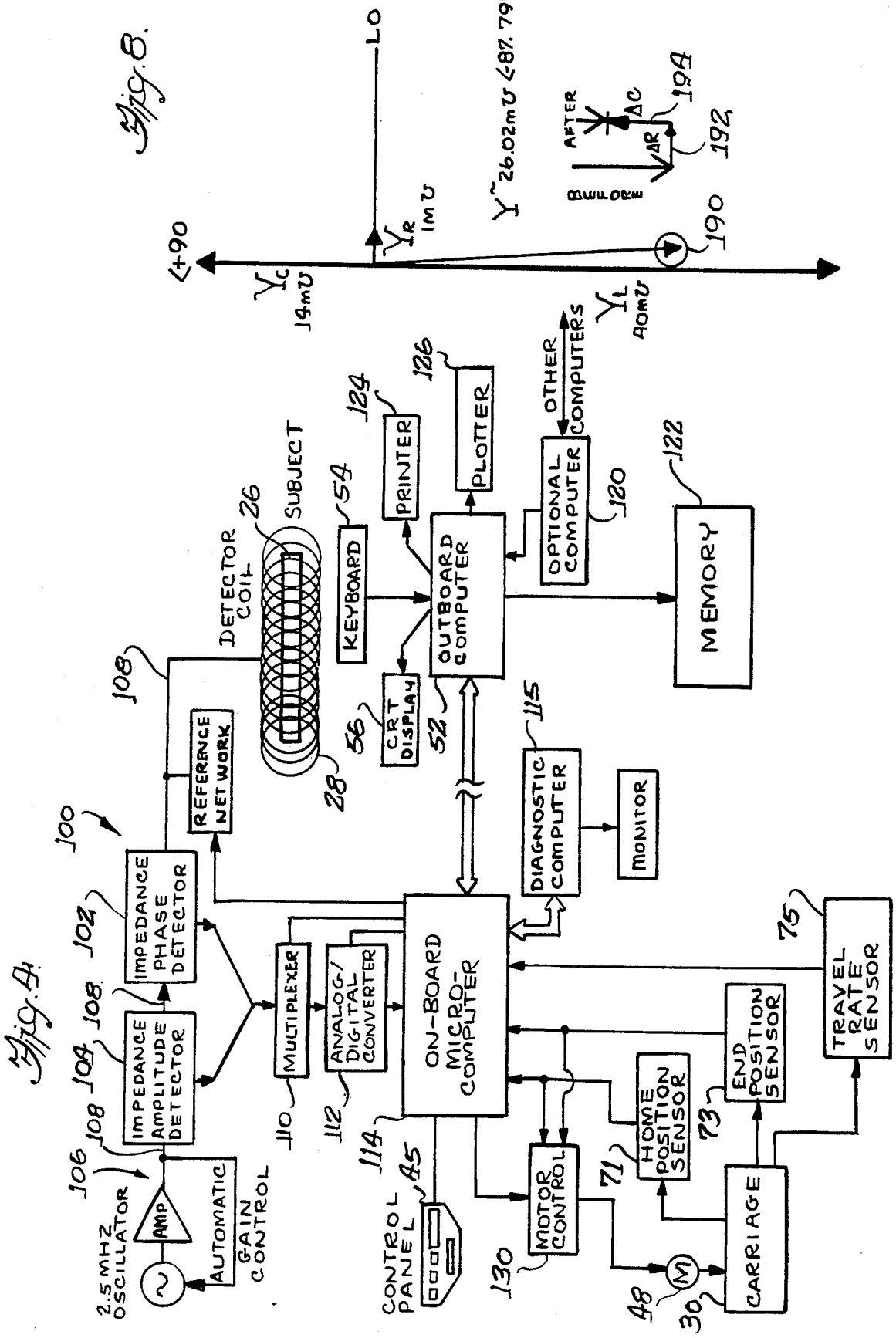

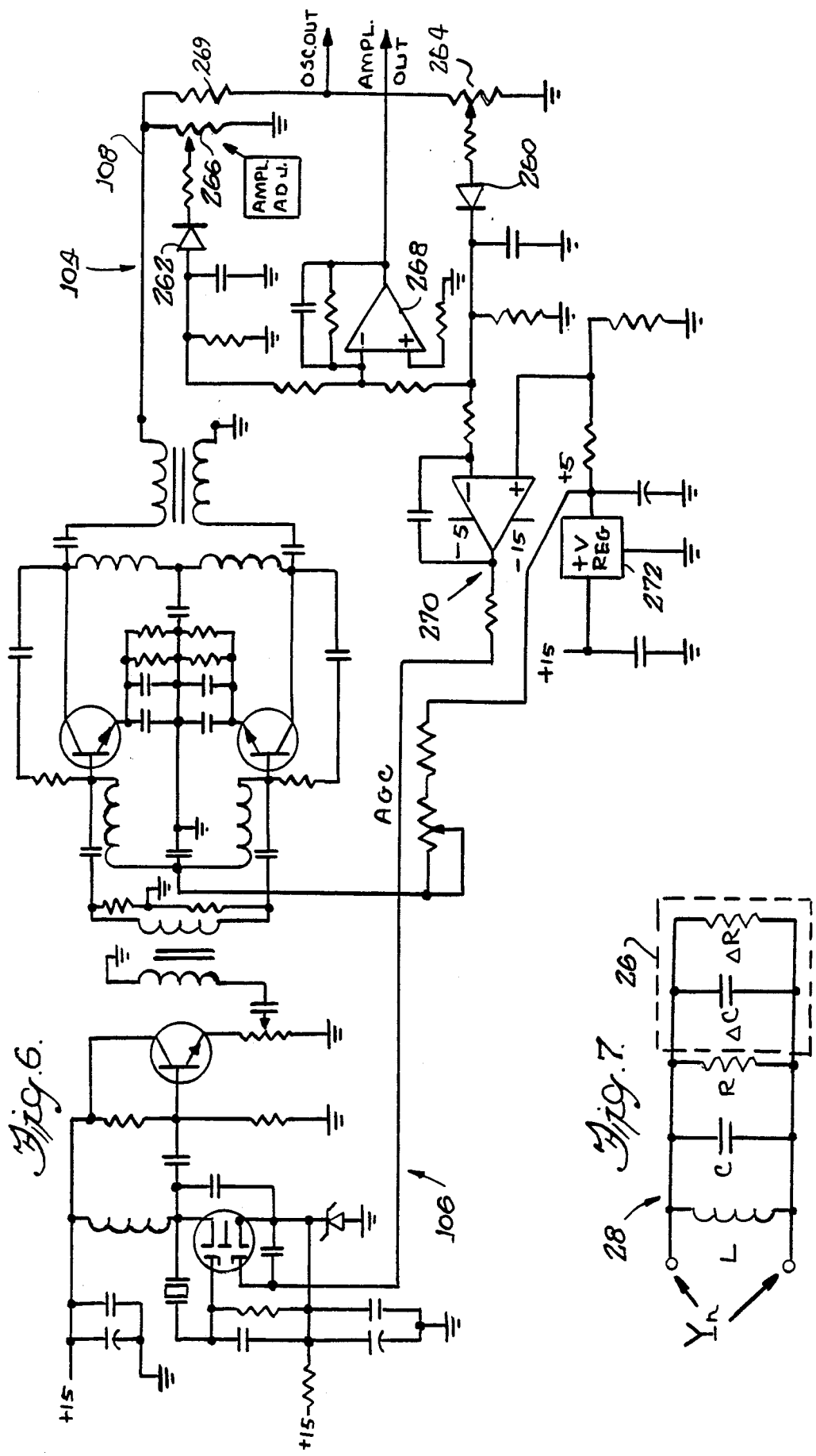

METHOD AND APPARATUS FOR MEASURING THE ELECTRICAL CONDUCTIVITY OF A SUBJECT

A computer program listing printout in the form of a "microfiche appendix" is being filed herewith.

BACKGROUND OF THE INVENTION

This invention is directed generally to the field of conductivity measurement and more particularly to a novel and improved apparatus and method for measuring the electrical conductivity of a subject by measuring the conductivity of an electromagnetic field producing element or elements, with the subject of interest being placed in the electromagnetic field produced thereby.

The prior art has proposed a number of methods and apparatus for determining the electrical conductivity of a subject by field disturbance and measurement techniques. For example, Harker, U.S. Pat. No. 3,735,247 is directed to apparatus for measuring the fat-to-lean ratio of meat by placing a package or sample of the meat in an electromagnetic field generated by a solenoidal coil and measuring the load on a drive source for the coil. Similarly, International Patent Application No. PCT/US 81/00602, published as International Publication No. WO 81/03226 is directed to the generation of pictorial images of selected volume elements of materials by a tomographic technique. In this technique, the material is brought within the influence of a relatively low-strength electromagnetic field and subjected to plural preselected frequencies to produce output data which is used to generate an image reflective of the conductance properties of the selected volume elements.

The prior application of David B. Funk et al., Ser. No. 375,552, now U.S. Pat. No. 4,496,907, filed on May 6, 1982 discloses apparatus for non-destructively determining the ingredients of a sample and specifically for determining the fat-to-lean ratio in a sample of a meat product. This application discloses a field producing coil, the sample of interest being placed entirely within the field of this coil, and the electrical conductivity of the coil being measured both with the sample absent and the sample present within the coil. A microcomputer is then utilized to determine the fat-to-lean ratio of the sample, based upon impedance or conductivity measurements taken of the coil.

The present invention is directed particularly to the problem of determining the conductivity of a relatively large subject, such as a live human or large live animal subject. Hence, unlike the prior art patents directed to the measurement of fat and lean in a sample of meat, the subjects to which the present application is directed are relatively non-uniform in composition and do not lend themselves to physical isolation of relatively smaller representative samples for testing. Moreover, these live human and animal subjects will be non-uniform in size, dimensions, and composition and distribution of components from one to the next, and hence cannot be placed in a field for test purposes in a uniform fashion from subject to subject. Also, the subjects may move during testing, unlike the inanimate subjects addressed in some of the above-referenced patents.

I have discovered that relatively simple conductivity measurements taken in a relatively low energy magnetic field may be subjected to computer aided analysis techniques to determine much useful information concerning the composition of the subject and/or of various parts of the subject. Such relatively low energy testing may advantageously be carried out without any specialized site preparation, shielding, or the like and without fear of harm to the subject. In contrast, many high-energy techniques such as X-ray, nuclear magnetic resonance (NMR), and other similar techniques require highly specialized room or site preparation and/or shielding and may also pose some exposure risks to both subjects and equipment operators.

A number of problems have arisen with respect to the testing of human or large animal subjects by the above-mentioned low-energy magnetic field disturbance technique. For example, the prior art has assumed that the subject must be placed entirely within a uniform and continuous field to assure accurate and repeatable results. In this regard, it has been believed that field disturbances and other areas of non-uniformity, such as boundary conditions, can result in unpredictable variations in test results. Accordingly, it has been believed that the axial length of a magnetic field used for testing (and hence of a coil for producing this field) must be on the order of two times the length of the subject and that the radius thereof must also be considerably greater than the greatest transverse dimension of the subject.

This relatively long axial length is to assure that the subject, when centered in the field, remains relatively far removed from axial end boundary effects of the field experienced at ends of the field-producing element such as a coil. Similarly, the relatively large radius is to permit the subject to be placed substantialy centrally within the field in the radial direction, to avoid non-uniform boundary effects experienced in the regions relatively close to the inner surface of the field-producing coil.

In this regard, a cylindrical coil has been utilized. One such coil previously utilized was of such a size that a rectangular housing or enclosure therefor was on the order of 12 feet in length, 6 feet in height, and 5 feet in width. Such a size requirement makes such an apparatus difficult to construct and transport and erect on the site at which testing is to be carried out. Moreover, such an apparatus requires a relatively large room or area for testing and cannot be readily moved or transported to another room or area to carry out testing. Hence, it has been believed heretofore that the size required of such an apparatus limited its portability and usefulness.

A second problem which has arisen with the techniques and apparatus utilized in some of the foregoing patents is the relatively small amount of data or information obtained by taking but a single reading of the subject or sample placed entirely within the field producing coil. The above-referenced International Publication has suggested utilizing a plurality of preselected frequencies to provide additional output data, and in addition suggests providing relative movement between the sample and the field. However, as previously mentioned, it was also believed that the sample should be maintained entirely within a uniform region of a field to avoid unpredictable effects of non-uniform boundary conditions at edges of the field producing coil or other apparatus. Hence, with respect to the human testing apparatus, satisfying both requirements of moving the sample relative to the field and of maintaining the sample in a uniform portion of the field would require an even larger apparatus than mentioned above. Moreover, the use of multiple frequencies in apparatus for human testing raises a number of problems, in that each frequency utilized must be approved for such use by the Food and Drug Administration of the United States Government. Obtaining such approval can be a relatively complex and expensive procedure. Hence, it is preferable to minimize the frequencies utilized and preferably to utilize but a single frequency for measurement.

A third problem which has arisen is that of the stability of the detector apparatus. In this regard, the electromagnetic field generating element or coil, the drive circuit for this coil and the measuring or detecting circuit for measuring the conductivity or other electrical properties of the coil are subject to unpredictable changes in gain, response and the like. Such changes may occur both from measurement to measurement over a period of time and from instrument to instrument, that is, among a plurality of otherwise identically constructed test instruments. In this regard, the conductivity or other electrical properties of a given coil may change from time to time due to interference from various factors such as environmental changes, aging of components, and the like. Similar factors may also cause variations in the gain or other electrical properties of the circuits used to drive the coil or other field producing element. Similarly, the measurement or detection circuits will include a number of electrical and electronic circuit elements which may similarly vary from time to time with environmental effects, aging or the like, in gain, scaling factors, response and the like. Hence, it has heretofore been a difficult problem to assure stability of the detector and correspondent accuracy and normalization or repeatability of readings. The same factors also make standardization of readings from one instrument to another difficult to obtain. Such standardization and stability are important in assuring statistical validity of the results obtained over a period of time on a number of subjects and with a number of instruments.

OBJECTS AND SUMMARY OF THE INVENTION

Accordingly, it is a general object of this invention to provide a novel and improved apparatus for measuring the conductivity of a subject.

A more specific object is to provide an apparatus in accordance with the foregoing object for measuring the conductivity of a relatively large, live human or animal subject.

A related object is to provide apparatus in accordance with the foregoing object which is of relatively small size compared to prior art apparatus for this purpose.

A further related object is to provide an apparatus in accordance with the foregoing objects which utilizes a relatively low level of energy so as not to require any specialized site or room preparation.

Another object is to provide an apparatus in accordance with the foregoing objects which is capable of producing a plurality of readings or data points in the testing of a subject.

A further object is to provide an apparatus in accordance with the foregoing objects which substantially solves the prior art problems of stability, normalization and standardization and consequently is capable with producing accurate, standardized and repeatable or normalized readings.

Briefly, and in accordance with the foregoing objects, apparatus for measuring the electrical conductivity of a subject comprises magnetic field producing means for producing a substantially uniform magnetic field within a predetermined volume; motive means for causing relative movement between said subject and said volume so as to move at least portions of said subject into and out of said volume; measuring means coupled with said magnetic field producing means for measuring the electrical conductivity thereacross; and control circuit means for causing said measuring means to measure the electrical conductivity across said field producing means a plurality of times while said subject is being moved relative to said volume so as to obtain a plurality of measurements of said electrical conductivity across said field producing means with said subject in said magnetic field to a plurality of different extents.

In accordance with another aspect of the invention, a method for measuring the electrical conductivity of a subject comprises producing a substantially uniform magnetic field within a predetermined volume; causing relative movement between said subject and said predetermined volume so as to move at least portions of said subject into and out of said volume; and measuring the electrical conductivity across said magnetic field a plurality of times during movement of said subject relative to said volume so as to obtain a plurality of measurements of the electrical conductivity across said magnetic field with different portions of said subject within said volume.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in the several figures of which like reference numerals identify like elements, and in which:

FIG. 1 is a perspective view of apparatus in accordance with the invention;

FIG. 2 is an enlarged side elevation, partially broken away of the apparatus of FIG. 1;

FIG. 4 is a block diagrammatic representation of the apparatus of the invention;

FIG. 6 is a schematic circuit diagram of an oscillator and amplitude detector circuit portion of the invention;

FIG. 7 is a diagrammatic representation of the impedance of a detector coil of the invention and of a subject within the coil, in equivalent circuit schematic form;

FIG. 8 is a graphical representation of the equivalent admittance of the impedance elements shown in FIG. 7;

DETAILED DESCRIPTION OF THE ILLUSTRATED EMBODIMENT

Figure 3:
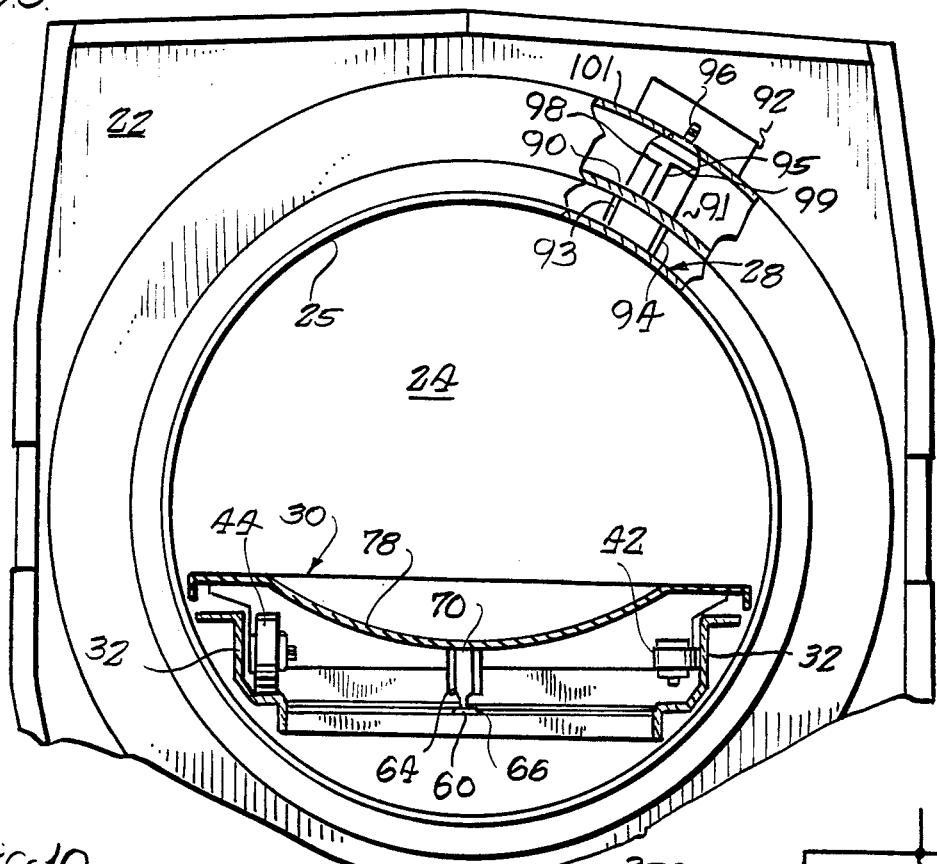
FIG. 3 is an enlarged partial front elevation, partially in section, of the apparatus of FIGS. 1 and 2.

Referring now to the drawings and initially to FIGS. 1 through 3, apparatus for measuring the conductivity of a subject in accordance with the invention is designated generally by the reference numeral 20. The apparatus 20 includes a housing 22 defining an open-ended, generally cylindrical chamber 24 for receiving a subject 26 therein. Magnetic field producing means in the form of a generally cylindrical coil means or detector coil 28 substantially surrounds the interior volume defined within the chamber 24. This coil 28 is arranged for producing a substantially uniform magnetic field within the volume defined in chamber 24.

Motive means are additionally provided for effecting relative movement between the subject 26 and the chamber 24. In the illustrated embodiment, the motive means takes the form of a carriage 30 which is movable or slideably mounted with respect to the chamber 24 and drive means 46 for driving the carriage. More particularly, the carriage 30 is mounted for slideable movement along a track 32 which in turn forms part of a base 35 at a first open end 25 of the chamber, for slideably mounting the carriage 30. A similar track 34 within chamber 24 aligns with and forms an extension of this track 32 for permitting further slideable movement of the carriage 30 along track 34 into and out of the chamber 24. A additional track extension 36 may also be carried upon a further separate base member 38 which may be aligned with an opposite end opening 40 of the chamber 24.

To this end, horizontal and vertical guide wheels or rollers 42 and 44 are provided on carriage 30 for riding in tracks 32, 34 and 36 as best viewed in FIG. 3. The drive means 46 includes an elongate tape 60 which is coupled by a coupling structure or arrangement, to be described later, with the carriage 30 for drawing or driving the carriage bi-directionally in the directions for moving the subject into and out of the chamber 24. A motor 48 is provided for driving the tape 60. Hence, the carriage 30 and drive means 46 including tape 60 and motor 48 and coupling structure comprise motive means for moving the subject in the directions into and out of the chamber. A control panel 45 includes suitable controls for initiating and controlling the movement of carriage 30 along the tracks 32 and 34 relative to the chamber 24.

Reference is next invited to the drive structure for driving carriage 30, as illustrated in FIGS. 2 and 3. The motor 48 drives the elongate flexible tape member 60 by way of a sprocket 62. This tape 60 is preferably a relatively flat, dimensionally stable, yet flexible tape having perforations for driving by the sprocket 62. Tape 60 mounts a connector or coupling block member 64, forming a portion of the above-mentioned coupling structure, at a leading end thereof.

An elongate track or channel member 66 is provided for guiding tape 60 and connector block 64 along the length of the first base cabinet 35 and the housing 22, generally in parallel with the tracks 32 and 34. This latter channel or guide track 66 maintains the tape 60 in a substantially flat condition as it travels the length of cabinets 35 and 22. Additionally, a tape storage bin 68 is provided for storing the unused length or portion of tape 60 in a coiled condition as indicated generally by reference numeral 60a. The coupling structure also includes a pivoted, complementary coupling or block 70 which has an end received in member 64 and is coupled by an elongate rod 72 to a second, similar pivoted coupling member or block 74. The block 74 is also pivotally mounted and coupled to be pivoted in response to similar pivotal motion of a handle 76 which extends outwardly of the housing or base member 35 for grasping by an operator. This handle 76 and the block 74 are also coupled with a trailing or head end of a frame member 78 of the carriage 30.

Hence, with the coupling structure or arrangement comprising elements 70, 72, 74 and 76 in the position illustrated in FIG. 2, rotation of the motor drives the tape 60 in the direction of housing 22, thereby pulling the carriage 60 generally from its head or trailing end into housing 22. The handle 76 is pivoted generally about a pivot 80 and may be pulled upwardly by an operator to release the coupling structure and thereby to permit manual return of the carriage to the position illustrated in FIG. 2. Briefly, upward pivoting of the handle about pivot 80 will be seen to cause pivoting in direction 82 by coupling or block member 74 by its pivot 84. Elongate rod 72 thus pulls on an upper portion of coupling 70 to cause it to pivot about its pivot point 86, thereby releasing its engagement with coupling 64.

Reference is next invited briefly to coil member 28, which in the illustrated embodiment comprises a plurality of generally flat, annular bands 87 of electrically conductive material in spaced apart alignment along the axial length of housing 22. These bands are interconnected at an upper side portion of housing to form a continuous coil member extending axially along the length of the housing 22. Electrical coupling between adjacent annular conductors is accomplished by relatively short "cross-over" conductors designated generally by reference numeral 88. However, the direction of current through the coil 28 thus defined is reversed for every third turn thereof by coupling adjacent annular conductor member ends directly together as indicated at reference numerals 89. That is, the axial direction of current flow is reversed every third turn while the azimuthal (i.e. around the circumference) direction of current flow remains the same.

Respective coupling points 89 are in turn joined together by elongate, axially running bus members 90 and 91. One of these buses 90 and 91 carries alternating signals from an oscillator to be described presently, while the other provides a ground bus. Hence, a drive signal and circuit ground are coupled to alternate ones of the couplings 89 along the axial length of the coil 28. These buses 90 and 91 run to a circuit portion of the measurement circuit of the invention carried in a housing 92 mounted at mid-point of the housing 22.

Referring also briefly to FIG. 3, the buses 90 and 91 will be seen to be coupled to the respective coupling points 89 of coil 28 therebelow by suitable radially running conductor members 93 and 94. A generally T-shaped frame member 95 carries conductors 98, 99 from the respective buses 90 and 91 upwardly into the circuit contained in housing 92, where the circuits are preferably carried into housing 92 by conductive threaded members or bolts 96, 97. These bolts 96, 97 pass through cylindrical shield 101 which extends the entire axial length of coil 28.

Referring again briefly to FIG. 2, respective position sensors comprising a home position sensor 71 and an end position sensor 73 are provided respectively in base 35 and in base 38 for detecting extreme positions of the carriage 30. Preferably, these sensors 71 and 73 comprises photoelectric type sensors. An additional travel rate sensor 75 may be additionally operatively coupled with motor 48 or sprocket 62 to detect the rotational speed thereof and therefore monitor the rate of travel of the carriage 30.

Referring to FIG. 1, in the illustrated embodiment an additional desk or table member 50 may extend from a side of the housing 22 to accommodate a small computer system 52 which includes a keyboard 54 and a video display 56. Advantageously, in the embodiment illustrated, the size of the chamber 24 is on the order of 80 inches in length by 30 inches in diameter. Hence, the housing 22, the carriage assembly and its base 35 (which is separable therefrom) as well as the extension track 36 and its base is which is also separable from housing 22, need not occupy an excessive amount of space. Moreover, as will be seen presently, since a relative low-energy magnetic field is generated by the detector coil 28, no specialized room or site preparation, shielding, or the like is required.

Referring now to FIG. 4, further features of the invention are illustrated in block diagrammatic form. The subject 26 is hereby illustrated entirely within the detector coil 28, that is, entirely within the volume defined within chamber 24. However, it will be appreciated from the following discussion that the subject may be within the chamber and hence within the coil to a greater or lesser extent. Moreover, to effect measurement of subject conductivity in accordance with the invention, measurements are preferably made with the subject within volume or chamber 24 to a plurality of different extents.

In accordance with the invention, measuring circuit means 100 are electrically coupled with the magnetic field producing means or coil 28 for measuring the electrical conductivity thereacross. It will be appreciated that the measured electrical conductivity of detector coil 28 will include the reflected conductivity due to the presence of any portion of the subject 26 therein. Accordingly, the conductivity of that portion of the subject 26 which is within the coil 28 may be derived or calculated by eliminating from the measurement that portion of the conductivity which is due to the coil 28 alone and any other factors other than the subject 26 which may affect the conductivity measurement.

Briefly, the measuring circuit means include a phase detector circuit portion 102 which is coupled with the coil 28 for producing a conductivity signal representative of the conductivity across the detector coil 28, including the reflected conductivity of any portion of the subject within the coil. An amplitude detector circuit portion 104 is coupled with the coil 28 for detecting the amplitude or magnitude of the admittance thereacross and producing a corresponding amplitude signal. In this regard, the detector coil 28 is energized or driven by an alternating electrical signal at a single frequency, provided from a 2.5 MHz oscillator circuit 106. The phase detecor and amplitude detector circuits are preferably coupled along a line 108 which feeds the oscillator signal from the oscillator 106 to the detector coil 28.

A selecting circuit means or multiplexer 110 is provided for alternately selecting the conductivity signal from phase detector 102 and the amplitude signal from amplitude detector 104. The signal selected at the multiplexer or selecting circuit means 110 is fed to an output circuit means comprising an analog-to-digital converter 112.

The analog-to-digital converter or output circuit 112 digitalizes the signal selected by multiplexer or selecting circuit means 110 and delivers the digitalized signals to an on-board microcomputer 114. This microcomputer 114 includes calculating circuit means responsive to the output signals from the converter 112 for calculating the conductivity of any portion of the subject 26 within the field of the detector coil 28. As previously mentioned, the conductivity of a portion of the subject within the coil 28 may be calculated by in effect eliminating the known effects of the detector coil 28 and any other extraneous factors influencing the gross conductivity reading taken there-across.

One method for determining only the conductivity of the portion of the subject within the coil in the above fashion is by utilizing background level subtraction and a "deconvolution" process. Briefly, such background level subtraction comprises a mathematical process for taking into account the influence of factors other than the subject on the conductivity reading made across the coil 28. This background level is due to the coil 28 itself, to the drive circuit for the coil or to other environmental or like factors affecting the magnetic field within the coil 28. Simply stated, a "convolution" of the magnetic field shape and the conductivity profile of the subject occurs during measurement due to the significant length of both the subject and the measurement fields. However, measurements taken across the coil 28 as carriage 30 is driven therethrough with no portion of subject 26 present, will determine the background level which may then be subtracted from the measurements with the subject 26 present. Similarly a measurement taken of the coil 28 with a known reference element placed therein can establish the "transfer function" of the coil. Once this transfer function is known, the reflected conductivity of any object placed within the coil can be deduced by "deconvoluting" the resultant measurement with the known transfer function. Such a process is particularly well carried out by a computer. In this regard, the on-board microcomputer might carry out this process or an additional "outboard" computer comprising the previously mentioned computer 52 might be utilized. When an additional outboard computer 52 is utilized this computer may be additionally programmed to derive other factors relating to the composition of the subject or of various parts of the subject. Outboard computer 52 may be additionally provided with a printer 124 and plotter 126 for producing hard copy records of measurements taken of any subject 26.

Further in accordance with a feature of the invention, the on-board microcomputer 114 includes control circuit means for causing the measuring circuit means 100 to measure the electrical conductivity across the field producing means or coil 28 a plurality of times while the subject is being moved in at least one of the directions into and out of the field in the volume defined by chamber 24. Hence, a plurality of measurements of electrical conductivity across the coil 28 are obtained with the subject in the field in the volume defined by chamber 24 to a plurality of different extents. From the foregoing, it will be appreciated that information relating to the conductivity and hence composition, of any given cross-sectional volume taken through the subject may also be determined. This may be done by comparison of the conductivity readings taken before the desired cross-sectional volume has entered the detector coil 28 with the reading taken immediately after the desired cross-sectional volume has entered the detector coil 28.

That is the effects of, the former reading may be essentially "subtracted" from the latter readings, by using a deconvolution method similar to that described above, to arrive at the reflected conductivity of the cross-sectional portion or volume of interest.

In accordance with the preferred embodiment illustrated, a "diagnostic" computer may also be coupled with on-board computer 114. Similarly, outboard computer 52 may additionally be coupled with one or more further and possibly remotely located computers such as an "optional" computer 120. This optional computer 120 may comprise either a computer similar to computer 52 coupled with a similar apparatus in another location, or a "main frame" computer at a remote location. Computer 120 could be used for storing cumulative data from the apparatus 20, and possibly, by way of telephone lines or the like from other apparatus similar to apparatus 20 at other locations. Computer 120 could also take the form of a data bank for use by on-site outboard computers such as computer 52 for calculating other factors of interest in the physical make of the subject. This would be done by correlating empirical data collected over a period of time and from a plurality of subjects. In this regard, additional memory 122 may also be provided for outboard computer 52.

In accordance with a further feature of the invention, the control circuit means portion of the on-board microcomputer 114 is coupled with the motive means for monitoring the position of the subject relative to the chamber 24. In this regard, the control circuit means includes synchronizing means for causing the measuring circuit 100 to measure the electrical conductivity across the magnetic field producing means or coil 28 at predetermined incremental positions of the subject relative to the chamber.

In the illustrated embodiment, the control circuit means are coupled with the motor 48 by way of a motor control circuit or motor circuit means 130. The home position sensor 71, end position sensor 73 and travel rate sensor 75 are also coupled intermediate the motive means (carriage, motor and drive) and control circuit means for sensing the position of the carriage and its rate of travel relative to the chamber 24. Accordingly, the control circuit means or portion of the microcomptuer 114 is responsive to the two position sensors and the rate sensor for determining the instantaneous position of the carriage relative to the chamber at any given time. The control circuit means thereby determines when the carriage 30 has reached incremental positions at which the measuring ciruit 100 is to be activated for measuring the conductivity across the coil 28.

Figure 5A:
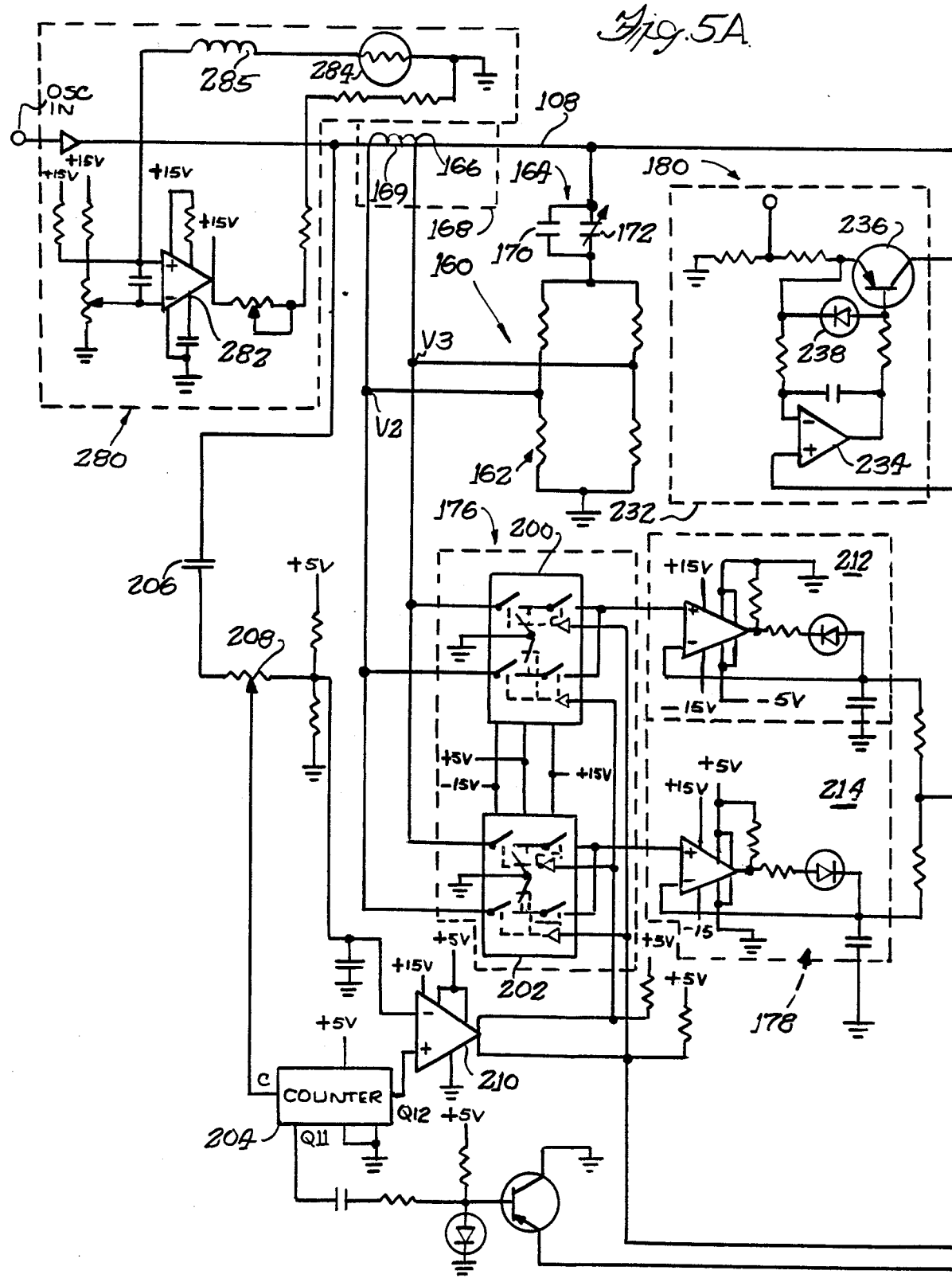
FIGS. 5A and 5B taken together form a schematic circuit diagram of a phase detecting circuit portion of the invention.
Figure 5B:
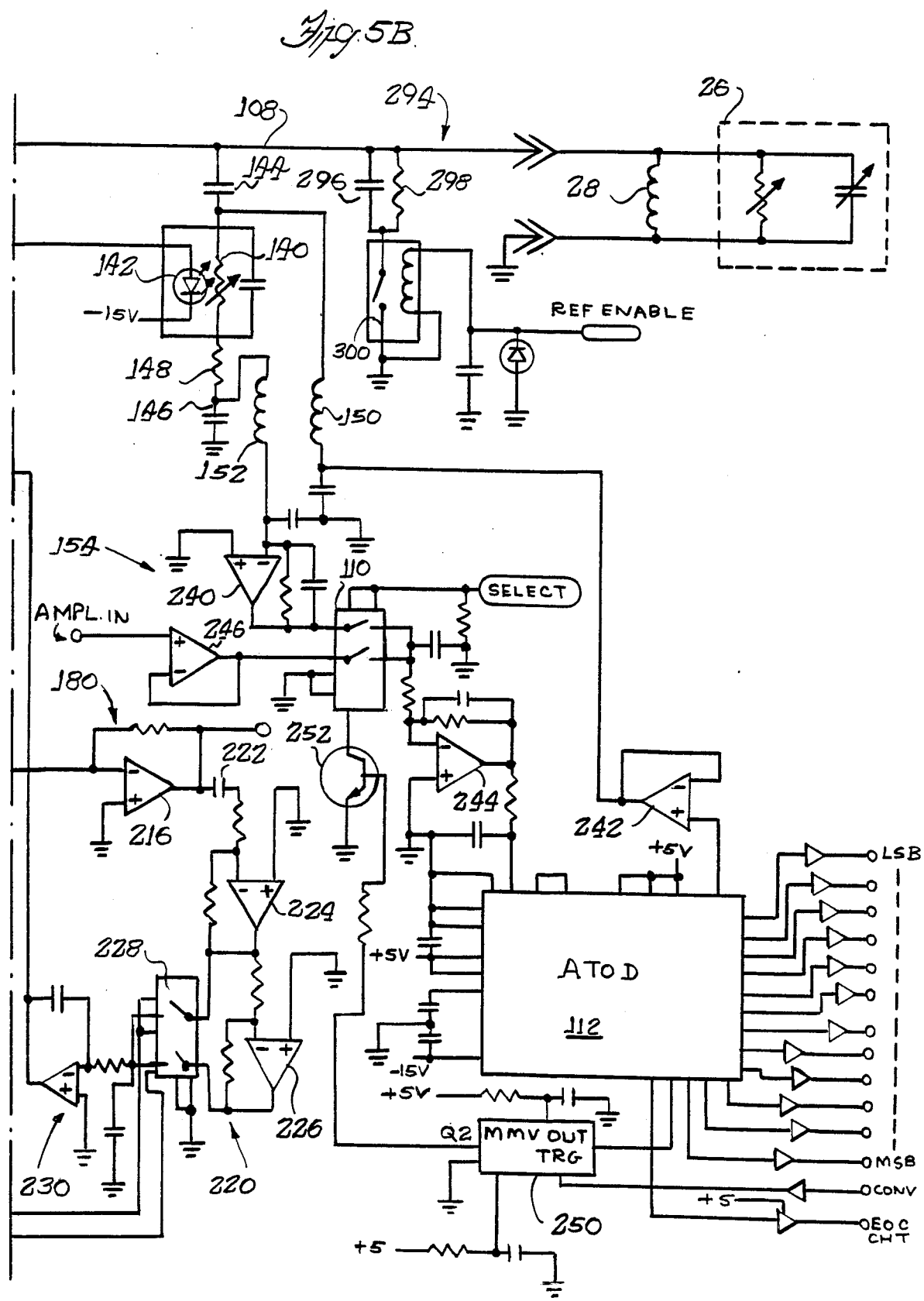

Reference is next invited to FIGS. 5A and 5B wherein details of the phase detector circuit means 102 are illustrated in schematic form. In accordance with a feature of the invention. the phase detector circuit means 102 comprises variable resistance means or a variable resistor 140 in parallel electrical circuit with the coil means or detector coil 28. In the illustration of FIG. 5B, detector coil 28 is symbolized in equivalent circuit form as an inductor, while the subject or portion of subject within coil 28 is symbolized in equivalent circuit form as the parallel combination of a variable resistor and a variable compacitor in parallel electrical circuit with coil 28. In this regard, it will be appreciated that the placement of a subject having both conductive and dielectric properties within the field of coil 28 will result in the reflected impedance or admittance of the subject appearing generally across the coil in equivalent circuit form substantially as illustrated in FIG. 5B.

Returning now to variable resistor 140, in the illustrated embodiment this variable resistor comprises a photoresponsive resistor which is preferably part of a circuit component also including an LED 142. Such a component is referred to as an LED vactrol component, for example, of the type VTL 5C available from Vactec, Inc., St. Louis, Mo. As will be seen presently, the LED 142 comprises a portion of a decoding circuit in a feedback control loop to the variable resistor or photoresistor 140.

Advantageously, the variable resistor 140 is AC-coupled in parallel electrical circuit with coil 28 by way of a capacitor 144 which runs from one end of resistor 140 to the aforementioned line 108 from the energizing oscillator A further capacitor 146 couples the other end of variable resistor 140 to ground by way of a further series-coupled resistor 148. In accordance with a further feature of the invention, the variable resistor 140 is further DC-coupled with a conductivity detecting and signalling circuit means 154. This DC coupling is accomplished by inductors 150 and 152 which are coupled respectively to the junctions of variable resistor 140 and first capacitor 144 and with second capacitor 146. In this regard, resistor 148 is preferably a precision resistor utilized to limit the maximum dissipation in variable resistor 140.

Advantageously, all conductivity readings are therefore taken from the variable resistor 140 coupled in parallel with the measurement coil 28, thus obviating the problems associated with drift, varying environmental influences and the like associated with reading the measurement coil 28 directly. Moreover, as will presently be seen, variable resistor 140 and LED 142 provide a closed-loop control system for additional stability and repeatability or "normalization" of the readings taken across variable resistor 140. These readings may be readily related to the conductivity of detector coil 28 including the reflected conductivity of any portion of subject 26 therein, which may then be determined as previously described, by background level subtraction and deconvolution. Measuring the conductivity of variable resistor 140 also eliminates problems with developing and reading a feedback or error signal directly which would render such a reading very sensitive to variations in gains, responses or the like throughout the intervening circuits, and hence make such readings difficult to normalize as well.

The phase detector circuit means 102 further includes an error detector circuit means designated generally by reference numeral 160 (see FIG. 5A). This circuit 160 is coupled with the detector coil 28 at line 108 for developing an error signal representative of the difference between the phase angle of the electrical admittance across the coil 28 and a preselected phase angle. In the illustrated embodiment, this preselected phase angle is a 90 degree phase angle, that is current lagging voltage by 90 degrees at coil 28. This 90 degree phase angle assumes the empty coil 28 to have an entirely inductive impedance or admittance.

Reference is now also invited to FIGS. 7 and 8. In FIG. 7, the impedance or admittance of the measurement coil 28 is represented by three elements: L, C and R, denoting an inductor, a capacitor and a resistor, in parallel electrical circuit. Similarly, the subject or portion thereof 26 within the coil is represented by the parallel combination of a capacitor and resistor, here designated as delta C and delta R in parallel with the inductive or admittance components of the coil 28. The net admittance of the foregoing elements is indicated across terminals of the coil 28 as Y.

In FIG. 8, the effect of these admittance components or elements of the coil on the net admittance vector thereof is illustrated. In the coil of the illustrated embodiment at the 2.5 Mhz frequency of oscillator 106, the admittance of the inductive element L of coil 28 alone was measured as substantially 40 millimhos, the conductance of the resistive component R thereof as substantially 1 millimho and the admittance of the capacitive component C as substantially 14 millimhos. Hence, the resultant admittance vector of the coil 28 alone (i.e., without any any portion of the subjct present) is calculated to be substantially 26.02 millimhos with a phase angle of minus 87.797 degrees, as symbolized by Y in FIG. 8. From this vector analysis, it will be appreciated that the addition of the resistive or conductive and dielectric components R and C of sample 26 will result in further changing of both the net length and relative phase angle of the admittance vector Y taken across the coil.

It will be noted in this regard that it is assumed that the subject for purposes of the measurement apparatus of the invention does not include any ferromagnetic material. In this regard, all ferromagnetic materials are kept out of the area of the measurement volume or chamber 24. Accordingly, the previously described carriage, as well as the tracks, rollers. drive tape and guide channel and coupling assembly are all of non-metallic material. Hence, the subject is here representativeby only resistive and dielectic components.

The error detector circuit means 160 responds to both the current fed to the coil along line 108 and the voltage across the coil, from which the phase angle between voltage and current and hence phase angle of the admittance of the coil may be derived. In this regard, the error detector circuit 160 includes a resistive bridge circuit 162, a top end of which is coupled with the line 108 by way of a phase null circuit 164 to be described later, and a bottom end of which is coupled to ground.

A pair of voltages representative of the current fed to the coil 128 along line 108 are developed at either end of the secondary coil 166 of a transformer 168. The primary 169 of the transformer 168 comprises a single turn, which is essentially a straight wire in series with line 108. The secondary 166 in the illustrated embodiment comprises 20 turns of wire. The two ends of secondary 166 are coupled to the two mid-points of bridge circuit 162 to develop a pair of voltages V2 and V3. These voltages V2 and V3 represent the sum of the voltage across the coil and a voltage corresponding to the current to the coil, and hence contain information as to the phase angle between voltage and current and therefore the phase angle of the admittance across the coil.

It will be recalled that a 2.5 MHz sinusoidal oscillator 106 drives coil 28, and hence the voltage on line 108, as well as the voltages developed at each end of secondary 166 are sinusoids of the same period. Moreover, it will be recognized that the voltages at opposite ends of secondary coil 166 will be exactly 180 degrees out of phase with each other.

In operation, if the detector coil 28 were purely resistive, that is, having a 0 degree phase angle, its voltage will be in phase with its current. Accordingly, the voltage V2 would then be at a maximum, since both current and voltage portions from which it is derived are in phase. However, the voltage V3 would be at a minimum, since the voltage from which it is derived at secondary coil 166 is 180 degrees out of phase with the current therethrough, which in turn is in phase with the voltage across coil 108. However, if the detector coil 28 is purely inductive, then the current therethrough will lag the voltage by 90 degrees. Hence, voltage V3 will be substantially equal to voltage V2, since the voltages at both ends of secondary coil 166 will be out of phase by exactly 90 degrees with the voltage across the detector coil 28.

The error signal is taken essentially as the difference between voltage V2 and voltage V3, as will be seen presently, so that the error signal will reach a minimum value when the phase angle of the admittance of the detector coil 28 is detected as being substantially 90 degrees.

Referring again briefly to FIG. 8, it will be remembered that the admittance of the coil in the illustrated embodiment is not purely inductive and hence the phase angle thereof is not exactly 90 degrees. Accordingly, the phase null or adjust circuit 164, which comprises a fixed capacitor 170 and a variable capacitor 172 is interposed between line 108 and the top of the resistive bridge circuit 162. This latter adjustable capacitor 172 is adjusted to make the phase angle of the voltage at the junction of capacitor 172 with bridge circuit 162 substantially exactly 90 degrees out of phase with the current through line 108. This is done to obtain substantial equality between voltages V2 and V3 with no subject present, to establish the zero or minimum error or reference point for the circuit 160.

Referring now more particularly to FIG. 5A, the error detector circuit means 160 further includes chopper stabilized circuit means designated generally by reference numeral 176 for processing the signals of the pair of bridge signals or voltages V2 and V3. Peak detector circuit means designated generally by reference numeral 178 are coupled to the chopper stabilized circuit means for detecting the peak amplitudes of the processed signals and producing corresponding peak detector signals. These peak detector signals, which comprise the error signal, are fed to decoding circuit means designated generally by reference numeral 180 and shown partially in FIG. 5A and partially in FIG. 5B. It will be noted that the error signal thus developed is representative of the difference between the phase angle of the admittance across the coil and 90 degrees. Any variation from the 90 degree phase angle of empty coil 28, as set by circuit 164, may be assumed to be due to the reflected admittance of any portion of the sample which is within the field of the coil 28. The decoding circuit means are responsive to the error signal for varying the resistance of the variable resistor or photoresistor 140 so as to maintain the preselected phase angle (that is, 90 degrees) of the admittance across the measurement or detector coil 28. In this regard, the previously mentioned LED 142 comprises a portion of this latter decoding circuit means.

Finally, the conductivity measuring or signalling circuit means 154 is DC-coupled with the variable resistor 140, as previously mentioned for developing a conductivity signal representative of the conductivity of the variable resistor. This signal and more particularly, the change in this signal as will presently be described, is therefore representative of the conductivity across the detector coil 28, including the reflected conductivity of any portion of subject 26 located inside of the coil 28.

In operation, it should be appreciated that some residual error signal current (a "non-zero" operating point) will energize LED 142 for maintaining a nominal value of conductivity of variable resistor 140, even in the "zero" error signal condition of the circuit. That is, since the closed loop control cannot have an ideal or infinite gain, some small residual drive signal, even in the absence of a difference between voltages V2 and V3 which produces the error signal will be present. Advantageously, this feature produces a measureable "residual" conductivity of resistor 140 to provide a reference point for measurement of conductivity across the coil 28 when the sample 26 or portion thereof is introduced into the coil. That is, with some nominal conductivity value of resistor 140 in circuit with coil 28, the circuit of FIGS. 5A and 5B will reach a essentially "balanced" or minimum error signal condition. Accordingly, when a sample or portion thereof is introduced into coil 28, it will cause the phase angle of the admittance thereof to decrease somewhat.

In this regard, reference is again invited to FIG. 8. Here the effect of elements delta R and delta C of FIG. 7 on the impedance of coil are shown in a somewhat enlarged view of the area of the end of vector Y as indicated by circle and arrow 190. It will be noted that the primary effect of the delta R vector is to decrease the phase angle somewhat in the direction of zero, that is, to move the phase angle farther away from the purely inductive negative 90-degree phase angle. It is this resistive or conductive component of the sample that is of interest. This component is indicated by reference numeral 192 in FIG. 8. Any dielectric component of the sample can be assumed to be relatively small compared to the admittance of the coil. Hence, with the phase angle of the coil substantially near 90-degree phase, and the phase angle of a dielectric or capacitive component being 180 degrees opposite, it will be seen that the primary effect of a small dielectric component delta C, as indicated by reference numeral 194 in FIG. 8, will be to decrease the magnitude or length of the net admittance vector Y.

With the change in phase angle due to addition of conductivity vector 192, voltages V2 and V3 will differ by some amount, causing an error signal to be produced. As will be described presently, the error signal is converted to a current for decreasing or subtracting from the residual current to LED 142 to thereby increase the resistance of photoresistor 140. In this regard, photoresistor 140 has a negative characteristic. Hence, the conductivity of photoresistor 140, which is the quantity measured by circuit 154, will decrease until the circuit is again in balance. This means that the conductivity of resistor 140 must decrease by the same amount as the net increase in conductivity due to the portion of sample or subject 146 within coil 28, that is, the conductivity vector 192 or delta R. Accordingly, by comparing the beginning and ending conductivity of variable resistor element 140, the difference therebetween can be ascertained. This difference must therefore be substantially equal to the conductivity component of the admittance of the portion of sample 26 introduced into coil 28.

Referring now to the circuits of FIGS. 5A and 5B in greater detail, the chopper stabilized circuit means 176 will be seen to comprise a pair of similar chopper circuits 200 and 202, each coupled to alternately select between the signals V2 and V3 from the bridge 62. A complementary chopper control or drive means is provided in the form of a counter or divider circuit 204. This counter 204 is AC-coupled by way of capacitor 206 and a current limiting variable resistor 208 to receive the 2.5 MHz signal from oscillator 106. In the illustrated embodiment, the counter is a 12-bit binary counter, and the Q12 output thereof is utilized to drive the non-inverting input of a high speed comperational 210, which receives its inverting input from a resistive voltage divider. Accordingly, an about 600 hertz chopper signal is produced at the outputs of comparator 210. Preferably, the high speed comperational 210 has a pair of complementary outputs, thereby producing the periodic signal of about 600 hertz and its complement for controlling the chopping by respective chopper circuits 200 and 202. These complementary signals are fed to both chopper circuits in such a way as to cause chopper circuit 200 to alternate between selection of the signals of the pair of signals V2 and V3 in the reverse sequence of their selection by the other chopper circuit 202 and vice-versa.

The peak detector circuit means 178 comprises a negative peak detector 212 and a positive peak detector 214 coupled to receive the signals selected by the respective chopper circuits 200 and 202. Hence, the circuits 212 and 214 develop respective peak detector output signals corresponding to a positive peak of the signal selected by chopper circuit 200 and a negative peak of the signal selected by chopper circuit 202. These positive and negative detected peaks are combined or summed at the input of a summing amplifier 216 (see FIG. 5B), to form a combined peak detector signal which is fed to chopper decoding circuit means designated generally by reference numeral 220 and comprising part of the decoding circuit means 180.

It will be appreciated from the foregoing description that additional stability of error measurements and insensitivity to variations and gain factors and the like throughout the above-described circuits are obtained by the utilization of this chopper stabilized error detection technique. For example, any offsets, spurious signals or the like produced by preceding circuit components is substantially cancelled out, since the voltages V2 and V3 are respectively fed to two halves of each integrated circuit package comprising choppers 200 and 202. Hence, any errors, drifts or the like in the components of one-half of each chopper circuit 200 or 202 can be expected to be substantially the same as in the other half thereof and hence will cancel out during the chopping or alternating between halves. The chopper circuits 200 and 202 preferably comprise monolithic RF/video switch circuits of the type generally designated IH 5341 available, for example, from the General Electric Company Intersil Division.

The summed or combined peak detector signal output at summing amplifier 216 will be a square wave signal at some DC reference level provided by the foregoing circuits, and having an amplitude directly proportional to the difference between voltages V2 and V3, or the "error" voltage or signal. This latter, combined peak detector "net" error signal is AC-coupled after amplification by amplifier 216 to the chopper decoding circuit portion 220 by way of a capacitor 222. This AC-coupled signal will now comprise the same square wave signal at a zero DC reference level; that is, the amplitude of either the positive or the negative peak of the square wave will now be one-half of the peak-topeak amplitude of the square wave produced at summing amplifier 216. This signal is further amplified at a first amplifier 224 and inverted at an inverting unity gain amplifier 226.

The outputs of amplifiers 224 and 226 feed respective switches of an analog switch circuit 228, which in the illustrated embodiment preferably comprises an analog switch of the type generally designated LF 13333. The two switches of analog switch 228 are driven by one of the complementary chopper control signals from the comparator 210. Accordingly, the foregoing circuit components 222, 224, 226 and 228 comprise chopper decoding means 220 which are AC-coupled to the summing means or amplifier 216 and are responsive to the AC component of the combined peak detector signal for developing a corresponding decoded signal.

The switching circuit 228 thus comprises a further switching or chopper circuit coupled to be driven by one of the complementary signals from the chopper control means and coupled for selecting between the combined peak detector signal and the inverse thereof provided at respective amplifiers 224 and 226. This decodes the signals processed by the chopper stabilizing circuit and hence, circuit 228 is driven synchronously therewith for this purpose. The signal output of switching circuit 228 will thus comprise a DC level or a resultant or decoded error voltage proportional to the combined peak detector signal of the square wave produced at summing amplifier 216 as previously described. This synchronized switching also determines the sign of the error. The foregoing chopper-stabilized detector technique further eliminates any errors due to changes in the input offset voltages of peak detector circuits 212 and 214 and operational amplifier 216.

This resultant or decoded error signal is fed to an integrating amplifier circuit 230, which in accordance with the invention provides integral feedback control for driving LED 142 to adjust the conductivity of variable resistor 140. Importantly, such an integral control arrangement assures that variable resistor 140 will be driven by the cumulative error signals over time to achieve and substantially maintain a balanced condition of the circuit of FIGS. 5A and 5B. It is at this balanced condition that the conductivity of the variable resistor 140 will be measured by circuit 154 and utilized to calculate the conductivity of the portion of subject 26 within the detector coil 28 as previously described.

Referring again briefly to FIG. 5A, the integrating amplifier circuit 230 feeds a voltage-to-current conversion circuit 232 which together with LED 142 forms a last portion of the decoding circuit means 180. This voltage-to-current conversion circuit includes an operational amplifier 234, a PNP transistor 236 and a diode 238. The collector electrode of transistor 236 feeds the resultant error current signal to the LED 142 thus completing the control loop of the phase detector circuit of FIGS. 5A and 5B.

The selecting or multiplexer circuit 110 comprises an analog switch also preferably of the type LF 13333. This latter switch 110 is coupled, as previously mentioned, to receive the signals both from the output of the phase detector circuit 102 and an output of an amplitude detector circuit 104 to be described presently. The phase detector circuit output comprises a signal corresponding to the current through variable resistor 140. This current converted to a voltage and is coupled to one input of the switching circuit 110 by an operational amplifier 240 which receives this current through the previously mentioned inductor or coil 152.

The inductor or coil 152 provides a DC reference voltage to the opposite side of variable resistor 140. This DC reference is provided from an operational amplifier 242 which is coupled to receive a reference voltage output from the analog-to-digital (A to D) convertor circuit 112. In the illustrated embodiment, this A to D circuit comprises a 12 bit A to D convertor of the type generally designated ADC 80 AG-12. The A to D convertor 112 receives the signal selected by selecting means or switching circuit 110 by way of a further operational amplifier 244.

A further similar operational amplifier 246 receives the amplitude signal from the amplitude detector circuit 104 indicated at an input designated AMPL, IN and delivers this signal to switching circuit 110. The selection of one or the other of these two signals at switching circuit 110 is controlled by the on-board microcomputer which feeds a selection control signal to a SELECT input of the switch 110. A further control signal for switching of circuit 110 is provided by a one-shot or monostable multivibrator circuit 250. The one-shot receives a trigger (TRG) input from the microcomputer 114 and produces a first, control pulse output at an output terminal OUT to the A to D converter 112 and a second control signal at a Q2 output. This latter control signal is coupled by way of a transistor 252 to a control input of the switching circuit 110.

Referring now to FIG. 6, the detector circuit 104, as previously indicated, is located along line 108 which carries the output of the oscillator circuit 106 to the coil 28. It will be noted in this regard that oscillator circuit 106 is also illustrated in circuit schematic form in FIG. 6. Turning now to amplitude detector circuit 104, this circuit includes positive and negative peak detector portions including respective diodes 260 and 262. These peak detectors are coupled for determining positive and negative peaks of the oscillator signal as it is affected by the presence of coil 28 in the circuit with or without some portion of subject 26 within coil 28. To this end, respective diodes 260 and 262, which are preferably Schottky diodes, sample the signal at the oscillator output (OSC. OUT) by way of respective potentiometers 264 and 266. These latter potentiometers may be used as amplitude adjustment (AMPL ADJ) or an amplitude null adjustment to derive a desired signal level at the output (AMPL. OUT) of the circuit 104 when no portion of the subject is present within the detector coil 28. The amplitude measurement circuit 104 responds to changes in peak current through resistor 269 in series with line 108, thus indicating changes in the magnitude of the admittance of the load.

The positive and negative detector portions of the circuit 104 are coupled to a summing junction at an inverting input of an operational amplifier 268, whose output forms the output (AMPL. OUT) of circuit 104. This output feeds the non-inverting input (AMPL. IN) of operational amplifier 246 of FIG. 5B. The positive peak detector also forms part of an automatic gain control (AGC) feedback circuit to the oscillator circuit 106. This AGC circuit further includes an operational amplifier or comparator 270 which receives the output of the positive peak detector circuit at its inverting input and has its non-inverting input coupled to a DC reference provided by a positive 5 volt voltage regulator 272.

Referring again briefly to FIG. 5A, the previously mentioned transformer 168 is preferably provided with a temperature regulation means or circuit designated generally by reference numeral 280. This regulation circuit includes an operational amplifier 282 which is coupled in circuit with a thermistor 284 and a heating element 285 for regulating the temperature of transformer 168 so as to remain within a preselected relatively narrow range of temperatures.

Figure 12:
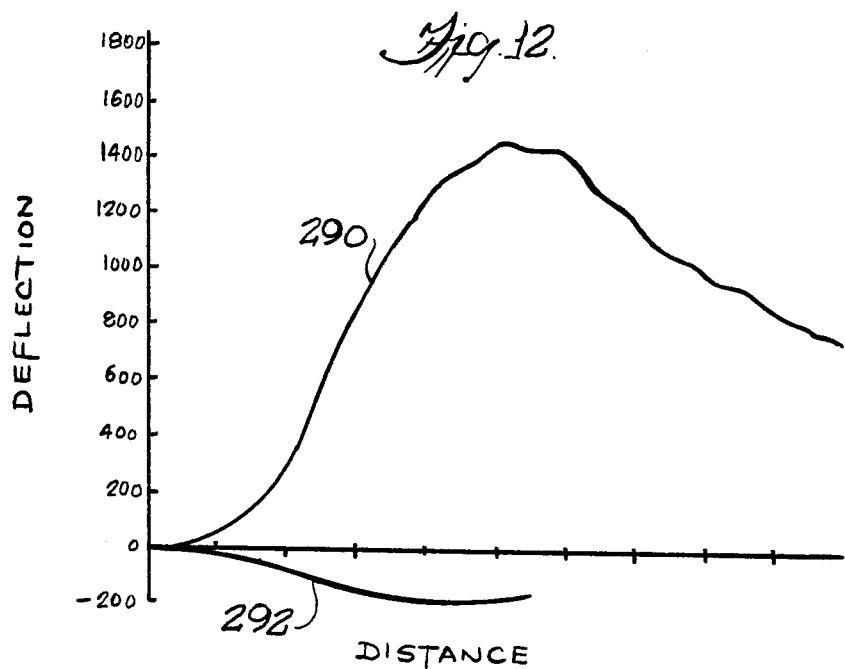
FIG. 12 is a graphic representation of a conductivity measurement of a subject made by the apparatus of the invention.

Referring briefly to FIG. 12, a graphic representation shows a series of connected measurement points forming curves 290 and 292 characteristic of the testing of a typical subject with the apparatus of the invention. As previously indicated, the taking of measurements corresponding to these plural measurement points is synchronized with movement of the carriage into and out of the chamber so as to obtain a plurality of readings of the subject, with the subject being in the field created by coil 28 in the chamber to a plurality of different extents. Specifically, these curves 290 and 292 represent plots of data points corresponding to the voltages respectively at the output of operational amplifier 240 of FIG. 5B and at the output of operational amplifier 268 of the amplitude detector circuit 104 of FIG. 6. It will be recalled that the output of operational amplifier 240 represents the conductivity of variable resistor 140, which comprises the output of phase detection circuit 102. The output of operational amplifier 268 represents the amplitude output signal of amplitude detector circuit 104.

As previously noted, the effects of the dielectric component of the subject or portion of the subject within the field of the detector coil 28 may be eliminated from the measurement by using the amplitude detector circuit. This circuit responds substantially only to the magnitude of the signal change and hence the magnitude of the admittance change of the coil 28 upon introduction of a portion of subject 26. As previously stated with respect to FIG. 8, with the phase angle substantially close to a purely inductive or a negative 90 degree angle, it can be assumed that a relatively small change in the dielectric or capacitance component of the admittance will result primarily in a change of the length or magnitude of the admittance vector. Hence, the circuit 104 responds only to the magnitude of the change of the oscillator signal which is correlative with the magnitude of the change in admittance. It will be recalled that the conductive or resistive change 192 described in FIG. 8 results primarily in a change in phase angle and has very little effect upon the amplitude or magnitude of the resultant admittance vector of coil 28.

To further normalize the readings obtained by the foregoing circuits, a reference circuit 294 is also utilized. This circuit comprises a capacitor 296 of known capacitance and a parallel resistor 298 of known resistance. These elements may be selectively switched into and out of the circuit by use of a reed switch 300 which is coupled to be selectively energized from a reference enable (REF ENABLE) output of the microcomputer 114. Accordingly, the microcomputer can further use the readings obtained from amplitude detector circuit 104 in response to these known or reference standard elements 296 and 298 being placed in the circuit to normalize the readings obtained during operation of this circuit in response to a subject. This reference circuit 294 may additionally be utilized to normalize the readings made by the phase detector circuit 102 as well as to merely check for continued accurate operation of the two circuits from time to time, if desired.

Figure 9A:
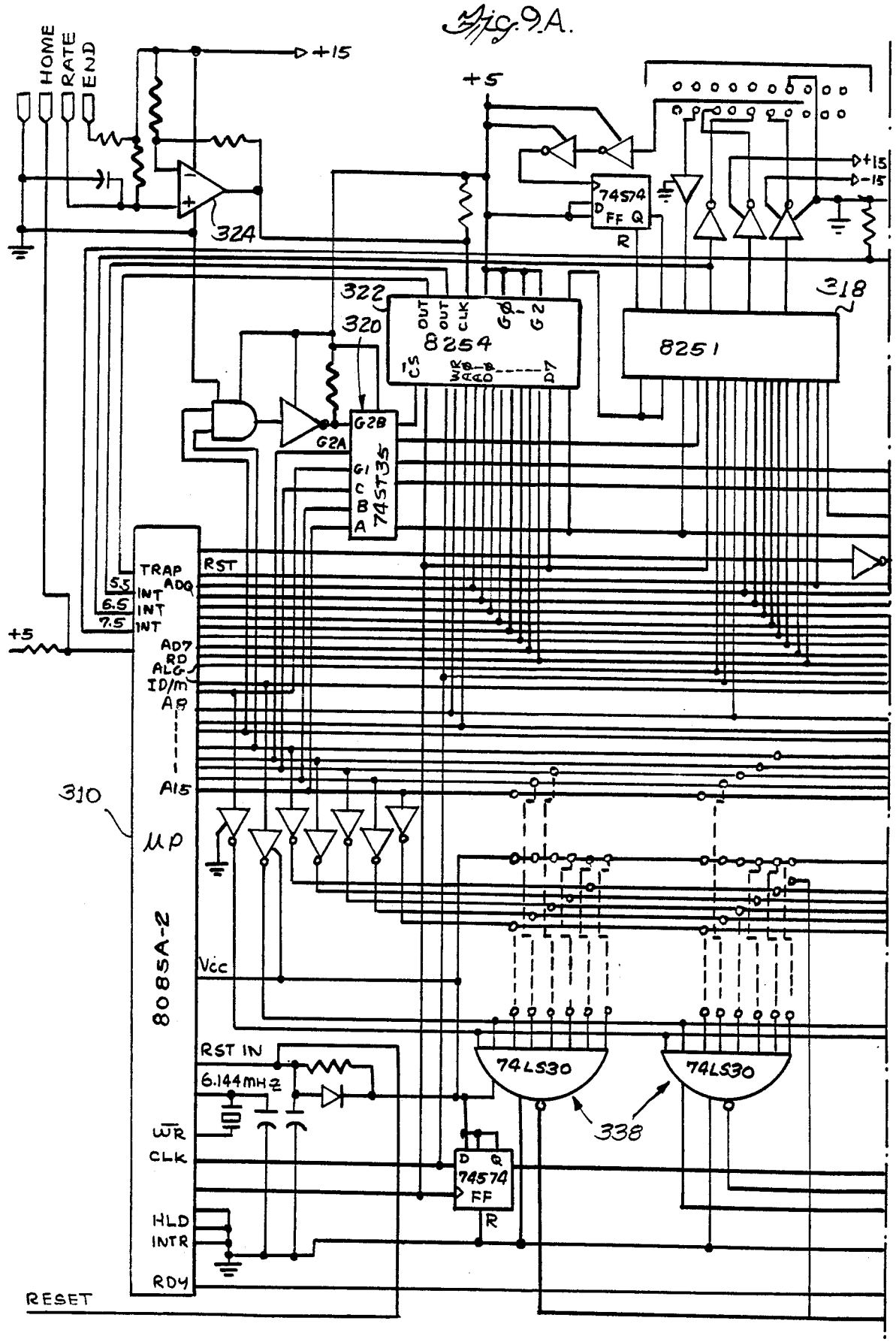
FIGS. 9A and 9B, taken together, form a schematic circuit diagram of a microcomputer circuit portion of the invention.
Figure 9B:
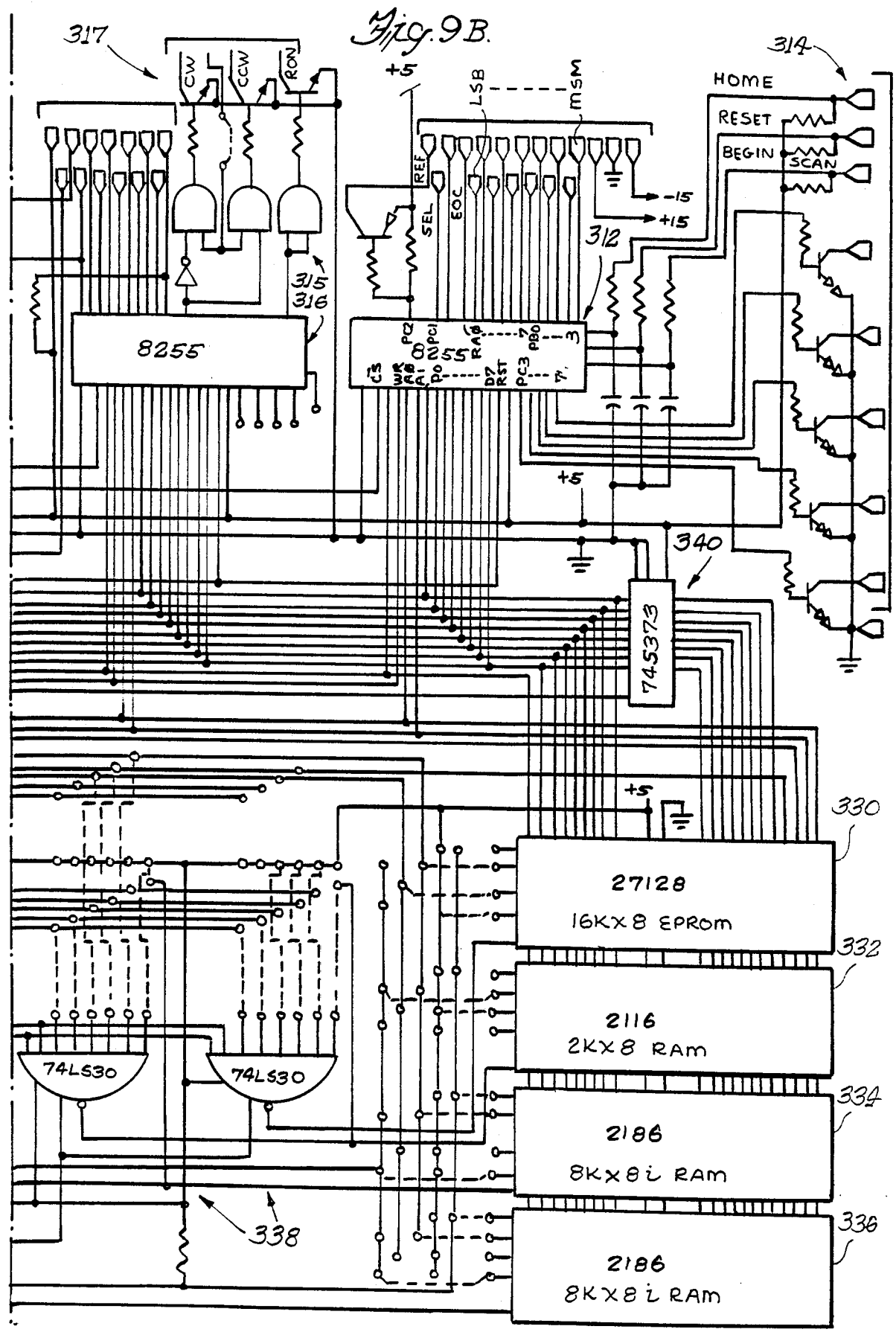

Referring now FIGS. 9A and 9B a schematic circuit diagram illustrates details of the microcomputer circuit 114 in accordance with a preferred embodiment of the invention. A microprocessor or microcomputer 310 comprises an integrated circuit microprocessor (uP) of the type generally designated 8085A-2. This microprocessor or computer 310 is coupled to receive the 12-bit output of the A to D converter 112 by way of an input/output (I/O) expander 312 of the type generally designated 8255. The 12 terminals over which this 12-bit information is exchanged are labeled as to the least significant bit (LSB) and most significant bit (MSB) respectively.

The I/O expander 312 also interfaces with the control panel 45 at a set of terminals designated generally by reference numeral 314. A second similar I/O expander 316, also preferably of the type generally designated 8255, interfaces between microcomputer 310 and the diagnostic computer 115 mentioned above.

Figure 11:
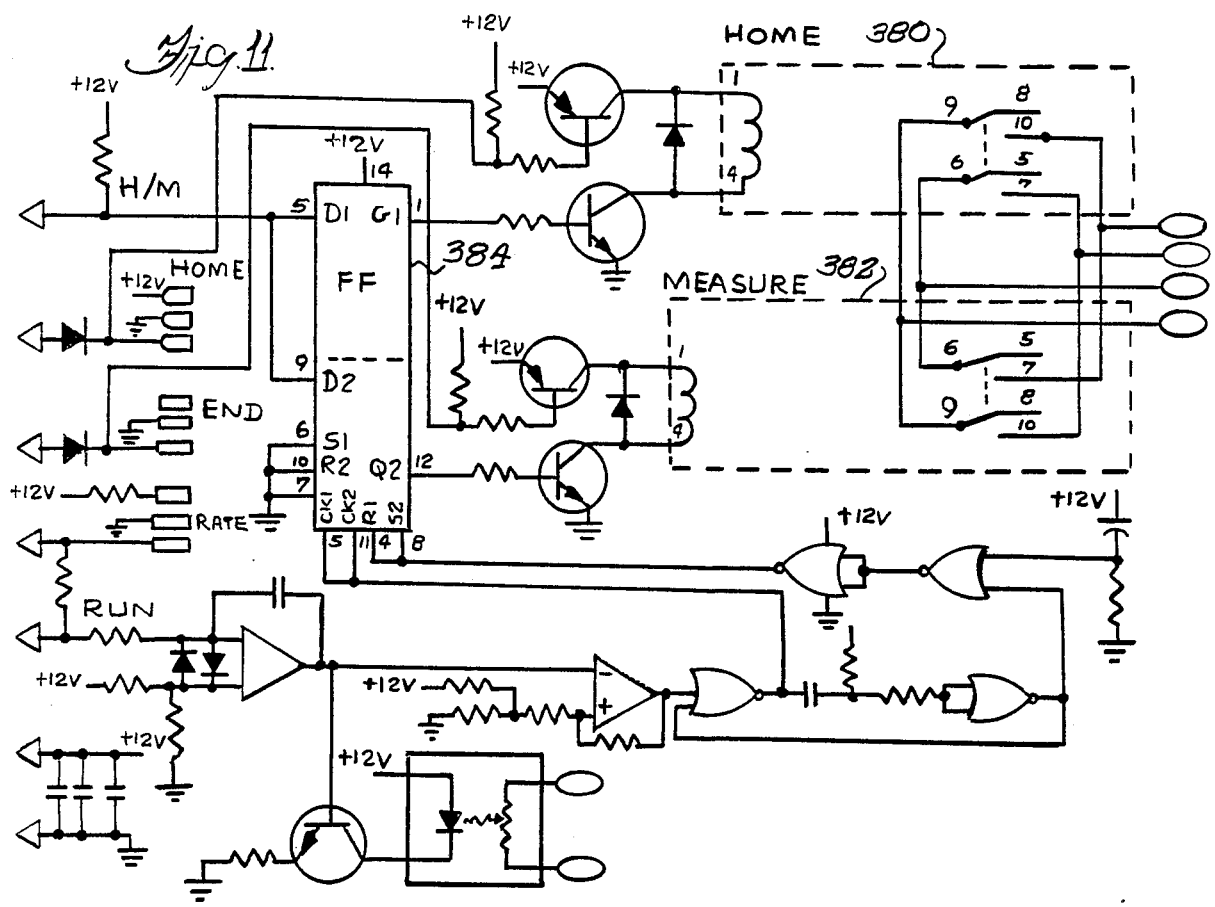
FIG. 11 is a circuit schematic diagram of a motor drive interface circuit of the invention.

The second I/O expander 314 also interfaces with the circuit of FIG. 11 by way of three gates designated generally by reference numeral 315 and series connected transistors designated generally by reference numeral 317 for controlling operation of the motor 48 for driving the carriage. In this regard separate controls are provided to run the motor (RUN) and for controlling clockwise and counterclockwise rotation, respectively (CW and CCW).

A further input/output circuit 318 comprises a universal asynchronous transmitter/receiver (UART), and preferably a type 8251 programmable communications interface available from Intel. This interface or transmitter/receiver circuit 318 provides interfacing between the microcomputer 310 and the outboard computer 52 described above with reference to FIG. 4.

Selection and control of the foregoing circuits by the microprocessor 310 is effected by a demultiplexer circuit 320 and a counter circuit 322. In the illustrated embodiment, the demultiplexer 320 is preferably a single, one of 8 demultiplexer of the type generally designated 74S1138, and counter 322 is preferably a triple, 16-bit binary counter of the type generally designated 8254.

The home position sensor 71, end position sensor 73 and travel rate sensor 75 are coupled to the microcomputer circuit of FIG. 9 at inputs designated generally HOME END and RATE, at the upper left portion of the circuit diagram. An interface circuit including an operational amplifier 324 is provided for the rate sensor input and preferably feeds into a clock input (CLK) of counter 322.

Memory capacity is provided in the form of a plurality of memory elements 330, 332, 334 and 336. In the illustrated embodiment, memory 330 comprises a 16K×8EPROM of the type generally designated 27128, which is an ultraviolet erasable and electrically programmable read only memory. The memory 332 comprises a 2K×8 static random access memory (RAM) preferably of the type generally designated 2116. The remaining memories 334 and 336 both comprise integrated or psuedo-static random access memories (iRAM) of an 8K×8 configuration, preferably of the type generally designated 2186.

A plurality of multiple-input gate circuits designated generally by reference numeral 338 are utilized to couple the memories in the desired configuration with the microprocessor 310. To this end a number of connections have been illustrated as jumper connections, to afford flexibility in selecting the memory configuration of the microcomputer circuit. An additional buffer circuit 340 of the type generally designated 74S373 is also utilized intermediate the address lines of the microprocessor 310 and some of the address lines of the memory circuits.

Figure 10:
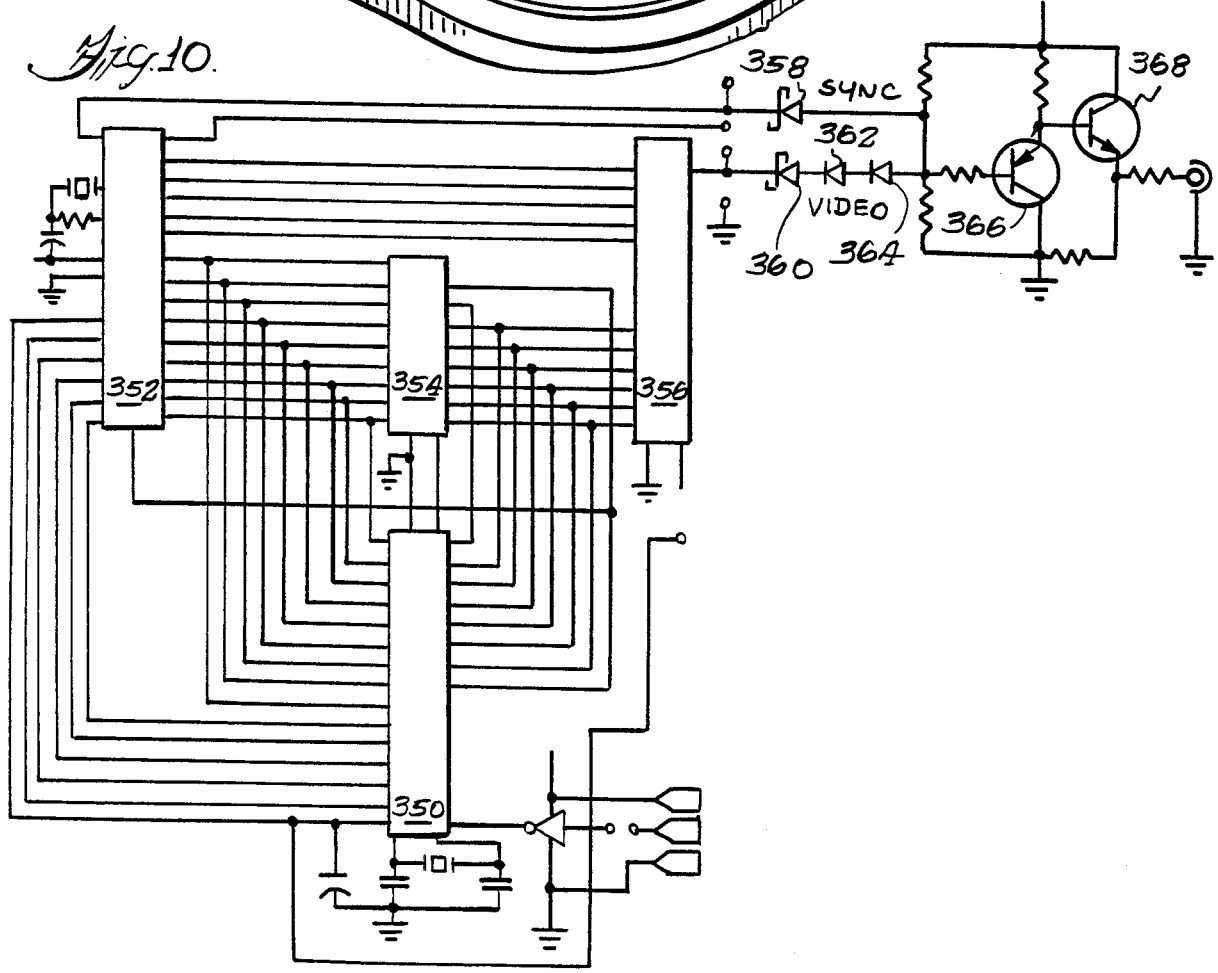
FIG. 10 is a schematic circuit diagram of a diagnostic computer circuit portion of the apparatus of the invention.

Referring briefly to FIG. 10, a diagnostic computer circuit is illustrated which may be utilized intermediate the outboard computer 52 and its video display 56 discussed above with reference to FIG. 4. Briefly, this circuit utilizes a single chip microcomputer circuit 350, preferably of the type generally designated 8049H. A programmable video controller 352 is also provided and is preferably of the type designated generally 8352. Suitable memory for this video interface circuit is provided by a memory 354 which in the illustrated embodiment preferably comprises a 2K×8 RAM of the type generally designated 2116, similar to the memory 332 discussed above. Finally, a character generator ROM 356, preferably of the type generally designated 86S64 is utilized and is interfaced both with the microcomputer 350 and the controller 352. Respective serial video and sync signals are carried out of controller 352 and character generator ROM 356 by way of circuits including HP2800 diodes 358 and 360, diodes 362 and 364, and transistors 366 (PNP) and 368 (NPN).

Referring to FIG. 11, a motor driver interface circuit is also provided. The motor driver interface circuit includes a home relay and a measure relay 380 and 382, which control operation of the motor 48 by way of the motor control circuit 130. The respective relays are in turn controlled from a flip-flop circuit 384, which in the illustrated embodiment comprises a dual-D flip-flop of the type generally designated 4013B. The flip-flop 384 is in turn controlled by the microcomputer for selecting between the home and measure relays 380 and 382. The home, end and rate sensors have respective inputs as indicated by the words HOME, END and RATE, to the motor circuit of FIG. 11 and are coupled directly therefrom to the microcomputer circuit of FIG. 9 as indicated by the like terms therein at the upper end left-hand corner of FIG. 9A.

While particular embodiments of the invention have been shown and described in detail, it will be obvious to those skilled in the art that changes and modifications of the present invention in its various aspects may be made without departing from the invention in its broader aspects, some of which changes and modifications being matters of routine engineering or design, and others being apparent only after study. As such, the scope of the invention should not be limited by the particular embodiments and specific constructions described herein but should be defined by the appended claims and equivalents thereof. Accordingly, the aim in the appended claims is to cover all such changes and modifications as fall within the true spirit and scope of the invention.

An exemplary program for operating the outboard computer 52 and the on board microcomputer 114 and particularly for the microcomputer or microprocessor portion 310 thereof is reproduced on microfiche in accordance with 37 CFR 1.96 as a "microfiche appendix".

The invention is claimed as follows:

1. Apparatus for measuring the electrical conductivity of a subject comprising: a chamber having at least one open end for receiving said subject therein; magnetic field producing means for producing a substantially uniform magnetic field within said chamber; motive means for causing relative movement between said subject and said chamber so as to move said subject into and out of said chamber; measuring circuit means electrically coupled with said magnetic field producing means for measuring the electrical conductivity thereacross; and control circuit means for causing said measuring circuit means to measure substantially only the electrical conductivity across said field producing means a plurality of times while said subject is being moved at least one of the directions into and out of said chamber so as to obtain a plurality of measurements of the electrical conductivity across said magnetic field producing means with said subject in said chamber to a plurality of different extents.

2. Apparatus according to claim 1 wherein said magnetic field producing means comprises coil means surrounding said chamber and wherein said measuring circuit means comprises phase detector circuit means coupled with said coil means for developing a conductivity signal representative of the conductivity across said coil means including the reflected conductivity of any portion of said subject located inside of said coil means and amplitude detector circuit means also coupled with said coil means for developing an amplitude signal representative of the amplitude of the electrical admittance across said coil means 3. Apparatus according to claim 2 wherein said phase detector circuit means comprises variable resistance means in parallel electrical circuit with said coil means, error detector circuit means coupled with said coil means for developing an error signal representative of the difference between the phase angle of the electrical admittance across said coil means and a preselected phase angle, decoding circuit means responsive to said error signal for varying the resistance of said variable resistance means for maintaining said preselected phase angle of said admittance across said coil means, and conductivity signalling circuit means for developing a conductivity signal representative of the conductivity of said variable resistance element, said conductivity signal corresponding in a predetermined fashion to the conductivity across said coil means including the reflected conductivity of any portion of said subject located inside of said coil means.

4. Apparatus according to claim 2 and further including selecting circuit means for alternately selecting said conductivity signal and said amplitude signal.

5. Apparatus according to claim 4 and further including output circuit means coupled to said selecting circuit means and responsive to the selected signal for developing a corresponding output signal.

6. Apparatus according to claim 5 wherein said measuring circuit means further includes calculating circuit means coupled to said output circuit means and responsive to said output signals for calculating the conductivity of any portion of said subject within said magnetic field.

7. Apparatus according to claim 1 wherein said motive means includes carriage means for receiving said subject and mounted for movement relative to said chamber, and drive means coupled with said carriage means for moving said carriage means into and out of said chamber.

8. Apparatus according to claim 1 wherein said control circuit means is coupled with said motive means for monitoring the position of said subject relative to said chamber and further includes synchronizing means for causing said measuring circuit to measure said electrical conductivity across said magnetic field producing means at predetermined,. incremental positions of said subject relative to said chamber.

9. Apparatus according to claim 8 and further comprising position sensor mean coupled with said motive means and with said control circuit means for sensing the position of said carriage means relative to said chamber and travel rate sensor means coupled with said drive means and with said control circuit means for sensing the rate of travel of said carriage means relative to said chamber.

10. Apparatus according to claim 9 wherein said drive means comprises motor means coupled for driving said carriage means and further including motor circuit means coupled with said control circuit means and with said position and rate sensor means for controlling operation of said motor in response to said control circuit means, said rate sensor means and said position sensor means.

11. Apparatus according to claim 10 wherein said control circuit means is further responsive to said position sensor means and to said rate sensor means for determining the position of said carriage relative to said chamber to thereby determine said incremental positions thereof at which said measuring circuit is to be activated for measuring said conductivity.

12. Apparatus according to claim 6 wherein said control circuit means and said calculating circuit means comprise computer means.

13. Apparatus according to claim 3 wherein said decoding circuit means comprises integrating circuit means coupled to said error detector circuit means for integrating the error signals produced thereby to form an integral control signal.

14. Apparatus according to claim 13 wherein said variable resistance means comprises a photoresponsive resistor and wherein said decoding means includes light emitting means mounted adjacent said photoresponsive resistor.

15. Apparatus according to claim 14 wherein said decoding circuit means further includes voltage-to-current converter means coupled intermediate said integrating circuit means and said light emitting means.

16. Apparatus according to claim 2 wherein said error detector circuit means comprises bridge circuit means coupled for response respectively to the voltage across said coil means and to the current to said coil means and for developing a pair of bridge signals corresponding in a predetermined fashion thereto, and chopper stabilized circuit means coupled to said bridge circuit means for processing said pair of bridge signals.

17. Apparatus according to claim 16 wherein said chopper stabilized circuit means comprises a pair of chopper circuits, each coupled to alternately select between the signals of said pair of bridge signals and complementary chopper control means for driving both of said chopper circuits with a pair of signals comprising a given periodic signal and its complement to thereby cause one of said chopper circuits to select between the signals of said pair of signals in the reverse sequence of their selection by the other of said chopper circuits.

18. Apparatus according to claim 17 wherein said error detector circuit means further includes peak detector circuit means coupled to said chopper stabilized circuit means for detecting the peak amplitudes of the processed signals and for producing corresponding peak detector signals.

19. Apparatus according to claim 18 wherein said peak detector means comprises a positive peak detector coupled for receiving the signals selected by one of said chopper circuits and producing a positive peak detector signal corresponding to a positive peak thereof and a negative peak detector coupled for receiving the signals selected by the other of said chopper circuits and developing a negative peak detector signal corresponding to a negative peak thereof.

20. Apparatus according to claim 19 wherein said detector means further includes summing means for combining said positive and negative peak detector signals to form a combined peak detector signal and wherein said decoding circuit means includes chopper decoding means AC-coupled to said summing means and responsive to the AC component of the combined peak detector signal for developing a corresponding decoded signal.

21. Apparatus according to claim 20 wherein said decoding circuit means further includes inverting amplifier means for inverting the combined peak detector signal to form the inverse thereof and wherein said chopper decoding means comprises a further chopper circuit also coupled to be driven by one of the complementary signals from said complementary chopper control means and coupled for selecting between the combined peak detector signal and said inverse thereof.

22. Apparatus according to claim 16 wherein said decoding circuit means comprises chopper decoding circuit means coupled to decode the signals processed by said chopper stabilized circuit means and driven synchronously with said chopper stabilized circuit means.

23. Apparatus according to claim 2 and further including oscillator means for driving said coil means with an oscillator signal of predetermined frequency and wherein said amplitude detector circuit means comprises positive peak detector circuit means and negative peak detector circuit means both coupled in circuit with said oscillator means and with said coil means for producing respective positive and negative peak detector signals in response to said oscillator signal, and summing amplifier means for summing said positive and negative peak detection signals and for amplifying the sum thereof to form said amplitude signal.

24. Apparatus according to claim 5 wherein said output circuit means comprises analog-to-digital converting circuit means.

25. Apparatus according to claim 3 wherein said error detector circuit means further includes phase angle correction circuit means for correcting the phase angle of the admittance of the coil means by a selectable phase angle correction factor when no part of said subject is present therein to thereby achieve said preselected phase angle.

26. Apparatus according to claim 3 wherein said error detector circuit means includes transformer means coupled in circuit for developing signals representative of the current to said coil means, and further including temperature regulation means coupled with said transformer means for regulating the temperature thereof so as to remain within a preselected relatively narrow range of temperatures.

27. Apparatus according to claim 3 wherein said preselected phase angle comprises a phase angle of substantially 90-degrees.

28. Apparatus according to claim 16 wherein said detector circuit means includes transformer means having a primary coupled in circuit with said coil means and a secondary coupled in circuit with said bridge circuit means to thereby develop a pair of voltages at said bridge circuit means representative of the current to said coil means.

29. Apparatus according to claim 28 wherein said detector circuit means further includes phase angle correction circuit means coupled intermediate said coil means and said bridge circuit for delivering a voltage to said bridge circuit representative of the voltage of said coil means with the phase angle thereof corrected to obtain said preselected phase angle of said admittance of said coil means with no part of a subject present within said coil means.

30. Apparatus according to claim 2 wherein said variable resistance means is AC-coupled with said coil means and DC-coupled with said conductivity signalling circuit means.

31. Apparatus for measuring the electrical conductivity of a subject comprising: magnetic field producing means for producing a substantially uniform magnetic field within a predetermined volume; motive means for causing relative movement between said subject and said predetermined volume so as to move at least portions of said subject into and out of said volume; measuring means coupled with said magnetic field producing means for measuring substantially only the electrical conductivity thereacross; and control circuit means for causing said measuring means to measure the electrical conductivity across said field producing means a plurality of times during movement of said subject relative to said volume so as to obtain a plurality of measurements of the electrical conductivity across said magnetic field producing means with different portions of said subject within said volume.

32. A method for measuring the electrical conductivity of a subject comprising: providing a chamber having at least one open end for receiving said subject therein; producing a substantially uniform magnetic field within said chamber; causing relative movement between said subject and said chamber so as to move said subject into and out of said chamber; measuring substantially only the electrical conductivity across said magnetic field a plurality of times while said subject is being moved at least one of the directions into and out of said chamber so as to obtain a plurality of measurements of the electrical conductivity across said magnetic field with said subject in said chamber to a plurality of different extents.

33. A method for measuring the electrical conductivity of a subject comprising: producing a substantially uniform magnetic field within a predetermined volume; causing relative movement between said subject and said predetermined volume so as to move at least portions of said subject into and out of said volume; measuring substantially only the electrical conductivity across said magnetic field a plurality of times during movement of said subject relative to said volume so as to obtain a plurality of measurements of the electrical conductivity across said magnetic field with different portions of said subject within said volume.

34. Apparatus for measuring the electrical conductivity of a subject comprising: a chamber having at least one open end for receiving said subject therein; magnetic field producing means for producing a substantially uniform magnetic field within said chamber; and measuring circuit means electrically coupled with said magnetic field producing means for measuring substantially only the electrical conductivity thereacross; wherein said measuring circuit means comprises phase detector circuit means coupled with said magnetic field producing means for developing a conductivity signal representative of the conductivity across said magnetic field producing means including the reflected conductivity of any portion of said subject located inside of said magnetic field producing means, and amplitude detector circuit means also coupled with said magnetic field producing means for developing an amplitude signal representative of the amplitude of the electrical admittance across said magnetic field producing means.

* * * * *